United States Patent [19]

Howe

[11] Patent Number: 5,168,240
[45] Date of Patent: Dec. 1, 1992

[54] CAPACITIVE FLUID PRESENCE DETECTOR FOR GAS PIPE USING AN EXCITED WIRE LOOP

[75] Inventor: Bradford H. Howe, Vergennes, Vt.

[73] Assignee: Simmonds Precision Products, Inc., Akron, Ohio

[21] Appl. No.: 743,748

[22] Filed: Aug. 12, 1991

[51] Int. Cl.⁵ .............................................. G01R 27/26
[52] U.S. Cl. ..................................... 324/690; 324/663; 324/686; 340/603
[58] Field of Search ............... 324/658, 663, 664, 686, 324/688, 689, 690; 73/61 R, 61.1 R; 174/11 R; 340/603, 604, 605, 632

[56] References Cited

U.S. PATENT DOCUMENTS

| | | | |
|---|---|---|---|
| 2,752,543 | 6/1956 | Smith | 324/690 |
| 3,569,824 | 3/1971 | Ruse | 324/439 |
| 3,635,082 | 1/1972 | Prellwitz et al. | 73/61 R |
| 3,662,367 | 5/1972 | De Veau, Jr. et al. | 174/11 R |
| 3,922,601 | 11/1975 | Martin, Jr. | 324/690 |
| 4,374,379 | 2/1983 | Dennison, Jr. | 340/605 |

Primary Examiner—Gerard R. Strecker
Assistant Examiner—Diep Do
Attorney, Agent, or Firm—David M. Ronyak; Leonard L. Lewis

[57] ABSTRACT

A liquid presence detector and method of using the same for a gas fluid pipe includes a helically wound insulated wire positioned inside the pipe such that an outer periphery of the wire contacts an inner surface of the pipe along an axial portion thereof. The pipe and wire form two plates of a capacitor with the pipe being connected to electrical ground for electromagnetic shielding and shock protection. The wire plate of the capacitor contacts liquid particles that travel along the pipe wall. A circuit is provided to measure capacitance between the wire and the pipe to detect liquid contacting the wire and pipe.

9 Claims, 3 Drawing Sheets

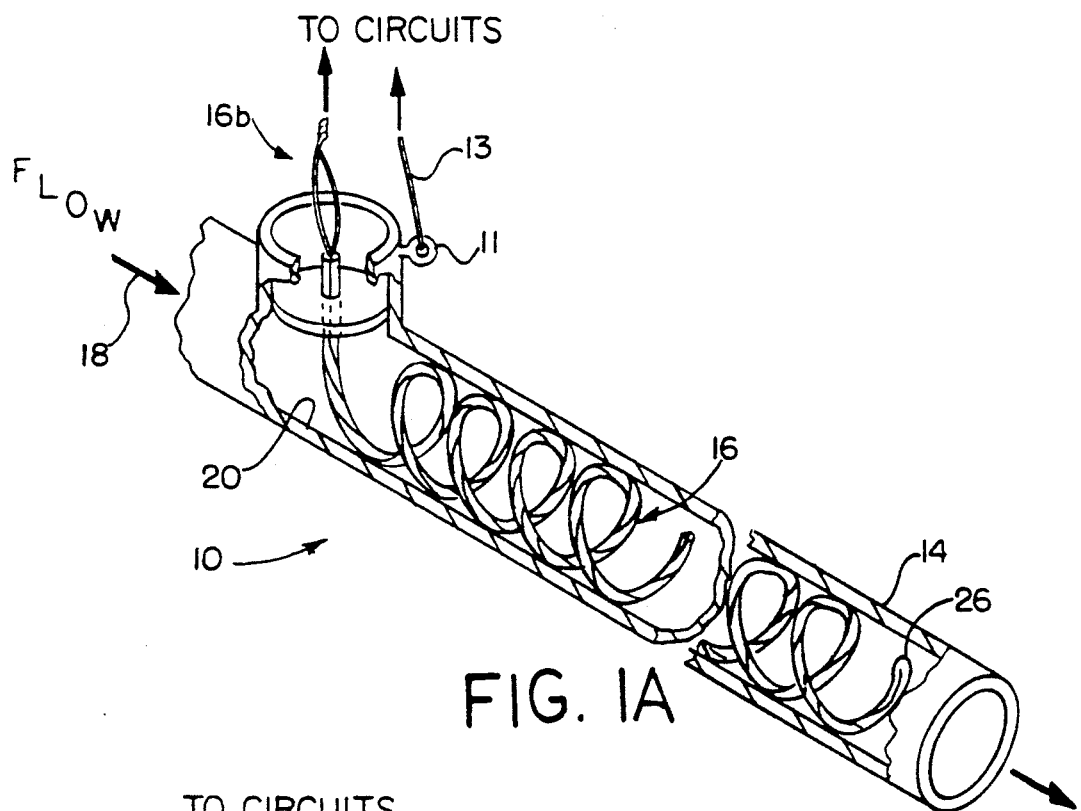
FIG. 1A
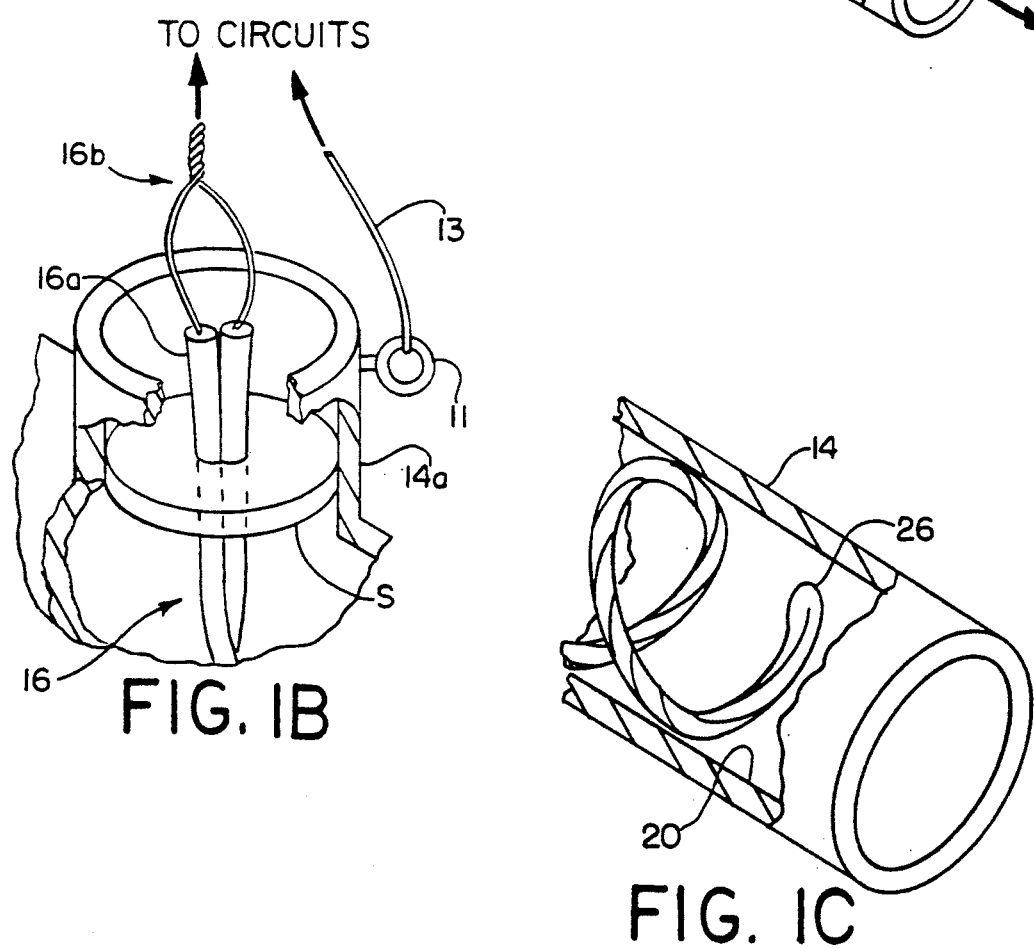
FIG. 1B
FIG. 1C

CAPACITIVE FLUID PRESENCE DETECTOR FOR GAS PIPE USING AN EXCITED WIRE LOOP

BACKGROUND OF THE INVENTION

The present invention relates generally to fluid conduits used to conduct or transport substances in gaseous form from one location to another. More specifically, the invention relates to providing a liquid presence detector for gaseous fluid conduits, which conduits are intended to function without the presence of liquid in the conduit.

Many types of apparatus require the use of gas-filled fluid conduits that are intended to operate with no liquid or condensate in the gas fluid. A typical example is a "gas only" output line for a water reclamation system. The presence of liquid in the gas line provides an indication that there is a leak or other failure in the separator apparatus. Liquids such as water can also be undesirable in gas feed lines. Water may occur due to direct leaks into the gas line, or from condensation of water vapor that is either present in the gas or that enters the conduit through some other means. A liquid recovery system or a liquid separator is typically included with such a gas line to extract the unwanted liquid. These liquid extraction systems may need to operate with an actuation signal that indicates to the system or an operator that liquid is present in the conduit or entrained in the gas. In highly controlled and sophisticated systems such as those used in connection with the space program, even small droplets of particles of liquids such as water can cause considerable damage to equipment. Furthermore, systems that are intended for use in space require a liquid detector that can function accurately and reliably in a substantially weightless environment.

A common problem with sensors and detectors that use electrical signals or properties such as resistance, capacitance and inductance is the presence of electromagnetic interference and general background electrical noise that cause false or erroneous readings. Such radiated noise can be coupled into a circuit and appear as false or spurious voltage and current spikes. This is especially true in space applications where there can be higher exposure to electromagnetic interference and radiation.

Another desirable feature of a liquid detection device is that it should be capable of detecting liquid that is traveling along the inner conduit surface or wall. Particularly in a weightless environment, the liquid particles tend to be pushed away from the primary gas towards the conduit wall, and then travel along the conduit wall under motive force from the gas moving through the conduit.

SUMMARY OF THE INVENTION

The present invention contemplates a liquid detector for fluid conduits that detects liquid particles that travel along the wall or inner surface of the conduit. The invention is particularly suited for use in conduits that carry gaseous fluids and are intended to be liquid free. The present invention also contemplates a liquid detector that can be used in a substantially weightless environment such as a space station, yet is relatively immune from the effects of electromagnetic interference and reduces the risk of electric shock.

The invention contemplates a liquid detector for a gaseous fluid conduit that utilizes the dielectric effect of liquids such as water to affect the capacitance of the detector. According to this aspect of the invention, the liquid detector includes a capacitor that has one plate formed from a piece of insulated wire positioned within the conduit and a second plate of the capacitor formed by the conduit. Portions of the wire physically contact the inner surface or wall of the conduit. When no liquid is present, the capacitance between the wire and the conduit is primarily a function of the wire insulation dielectric, and the length of the wire. When liquid such as water accumulates on the wire, the capacitance between the wire and the conduit changes due to the dielectric change caused by the liquid. One end of the wire is accessible from outside the conduit so that a capacitance measuring device can be connected thereto.

In the preferred embodiment, the wire capacitor plate is wound in the shape of a helix so that the wire has multiple loops that surround a central longitudinal axis of the conduit. According to this aspect of the invention, the wire functions as a liquid collector or trap for liquid that is traveling along the conduit wall. By providing at least one loop surrounding the conduit's longitudinal axis, the wire coil contacts and obstructs liquid particles traveling along the conduit wall regardless of the particular displacement of the liquid particle on the inner surface. In a weightless environment, liquid entrained in a gaseous fluid is forced towards the conduit wall and tends to collect on the wall and travel therealong, due to the force exerted on the particles by the flowing gaseous fluid. In a gravity environment, the force of gravity also tends to result in fluid particles collecting on the conduit wall. The liquid can further be forced against the conduit wall by including a bend in the conduit upstream from the liquid detector.

In accordance with another aspect of the invention, a liquid detection device for a gaseous fluid conduit is provided that uses the conduit as one plate of a sensor capacitor. Preferably, the conduit is electrically grounded, which has the benefits of both improving the shielding of the sensor capacitor from electromagnetic interference, as well as reducing the risk of electrical shock. The latter concern is particularly important in applications where personnel may be in close proximity to the conduit, and when the liquid is electrically conductive.

The present invention also contemplates a new method for detecting liquid particles in a gaseous fluid conduit. This method includes the steps of connecting the conduit to electrical ground; placing a helically wound insulated wire in the conduit along the longitudinal axis thereof in such a manner that an outer surface of the wire coil contacts an inner surface of the conduit to form a capacitor; using the helically wound wire to obstruct flow of liquid particles along the inner surface of the conduit such that liquid particles contact the wire; and measuring capacitance between the wire and the conduit to detect presence of liquid in the conduit.

These and other aspects and advantages of the present invention will be apparent to those skilled in the art from the following detailed description of the invention in view of the accompanying drawings.

BRIEF DESCRIPTION OF THE DRAWINGS

FIG. 1a is a perspective schematic in partial longitudinal section of a capacitive liquid presence detector for a gas conduit in accordance with the present invention;

FIG. 1b is an enlarged view of a portion of the device shown in FIG. 1a;

FIG. 1c is an enlarged view of another portion of the device shown in FIG. 1a;

DESCRIPTION OF THE PREFERRED AND ALTERNATIVE EMBODIMENT

Figure 1D:
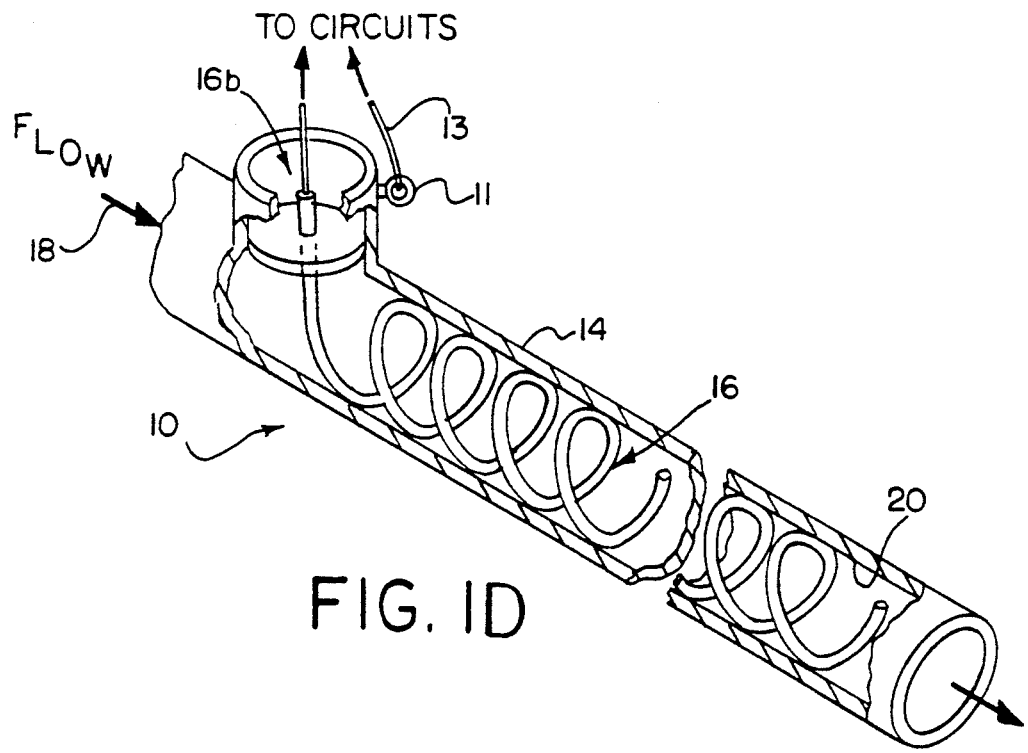
FIG. 1d is a perspective schematic in partial longitudinal section of an alternative embodiment of a capacitive liquid presence detector for a gas fluid conduit.

Referring to FIG. 1a, a liquid presence detector used in combination with a fluid conduit according to the present invention is generally indicated by the numeral 10. The detector 10 is preferably embodied in the form of a capacitor wherein a first plate or electrode 12 of the capacitor is the conduit 14. The conduit 14 may be pipe, tubing or the like that is used to contain and conduct gaseous fluid, for example, an "air only" output line from a water reclamation system in a space station. While the invention is shown and described herein with respect to a particular embodiment such as a gas-only fluid conduit, those skilled in the art will appreciate that the invention can be used in any system in which it is desired to detect the presence of liquid in a gaseous fluid conduit. It will also be appreciated that the present invention is not limited to the detection of water, but can be used to detect any fluid that measurably alters the capacitance of the detector 10. The present invention also is not limited to use in a weightless environment though such an application is one for which the present invention is particularly well suited.

Another plate or electrode 16 of the detector 10 capacitor is realized by a piece of insulated wire 16. The wire 16 is preferably formed into the shape of a helix and is placed inside the conduit 14. The helical wire 16 extends through a portion of the conduit 14 along the longitudinal axis 18 thereof. The wire 16 is sized and formed so that multiple turns of the wire directly contact an inner surface 20 of the conduit 14.

The conduit 14 is preferably made from an electrically conductive material such as aluminum or stainless steel. The conduit 14 is connected to electrical ground by any convenient means such as a grounding wire or cable (not shown).

As best shown in FIG. 1b, the wire 16 includes an insulative coating 16a in a known manner so that the capacitance between the wire 16 and the conduit 14 is a function of the length of the wire 16 and the dielectric constant of the wire insulator material. The capacitance is also a function of the thickness of the wire insulation and the total surface area of the wire in direct contact with the conduit. Precise control over these various parameters is not required because a reference or baseline value of the capacitor can be established by measuring the capacitance between the wire 16 and the conduit 14 under dry conditions i.e. conditions when it is known that there is no liquid contacting the wire.

The use of the conduit 14 as one plate of the detector 10 capacitor provides significant advantages, one of which is that the conduit can be electrically grounded. This is an important safety feature because capacitive sensors require an applied voltage or current to detect the capacitance during operation. Since the conduit is grounded, however, there is no risk of electrical shock to personnel that may come into contact with the conduit 14. Using the conduit as a capacitor plate also provides for a simple and compact capacitive sensor that is particularly well-suited for small diameter pipes.

The grounded conduit 14 also acts as a shield against electromagnetic interference that could otherwise be coupled to the wire 16 positioned within the conduit 14. Thus, the conduit serves both as an integral part of the liquid detector, as well as a shield to isolate the liquid detector from the electromagnetic effects of radiation and background noise.

In the example being described herein, the detector 10 is useful for detecting liquid particles in a gaseous fluid conduit intended to be liquid free. In particular, the coiled wire 16 functions to obstruct the movement or flow of liquid particles along the inner surface 20 of the conduit 14. The wire 16 may in fact capture or completely block the flow of liquid particles depending on such variables as the size of the wire, the size and quantity of the liquid particles, and the flow rate of gas through the conduit. The wire 16 may or may not be intended to capture the liquid particles depending on the particular application of the detector 10. But, in either case, the capacitive sensor detects the presence of liquid particles due to the change in dielectric characteristics when the liquid contacts the wire. In particular, in a weightless environment such as a space station, liquid particles tend to be thrown outwards towards the conduit wall due to the motive force of the gas fluid traveling through the conduit. Placing a bend (not shown) in the conduit 14 upstream from the wire sensor will also cause the liquid particles to travel along the conduit inner surface 20. The invention has been used successfully to detect water liquid particle sizes on the order of 0.05 cc at a flow rate of at least 1.5 cc per minute within an air conduit with the air passing through at a rate of at least 20 feet per second.

Figure 1E:
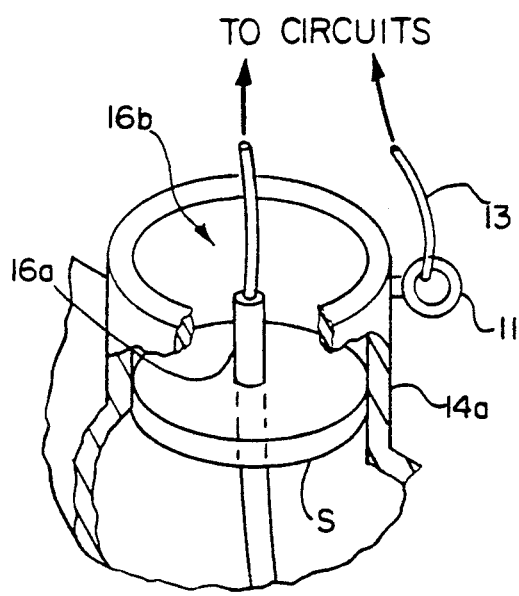
FIG. 1e is an enlarged view of a portion of the device shown in FIG. 1d.

The wire 16 may be a single strand wire as depicted in FIGS. 1d and 1e, or may be a multiple strand wire as in FIGS. 1a-1c, depending on the desired sensitivity of the capacitor. The multiple strand embodiment can be realized by simply folding a single wire back on itself as at point 26 in FIG. 1c. The use of folded multiple strands has the benefit of not requiring a seal for the exposed end of the insulated wire within the conduit 14.

As shown in FIGS. 1b and 1e, in either embodiment one end 16b of the wire 16 extends outside the conduit 14 as through a boss 14a, including the use of an appropriate seal S to block escape of the gas in the conduit. Of course, the wire can also be brought outside the conduit simply through a sealed hole or any other convenient way. The external end 16b of the wire can then be connected to a capacitance detecting circuit. A post 11 is provided to connect a grounded wire 13 thereto in order to provide a ground reference.

Figure 2:
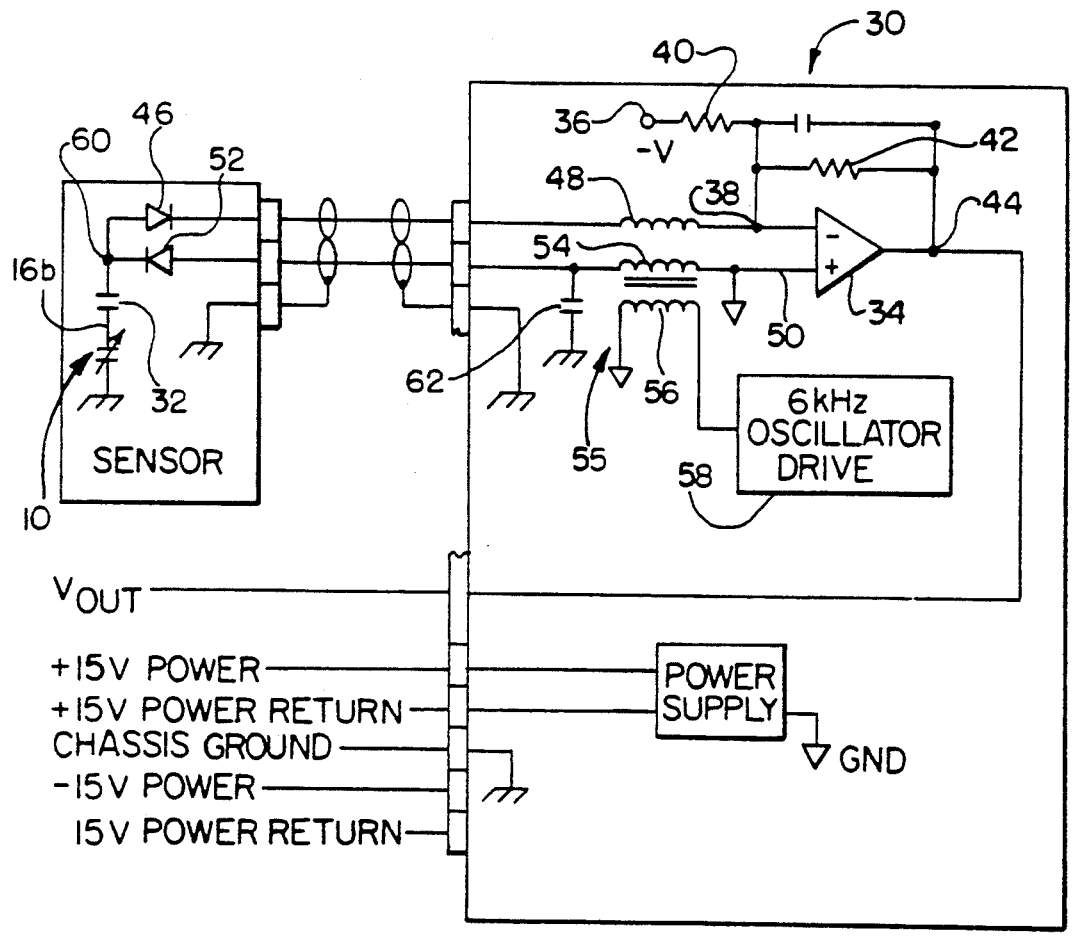
FIG. 2 is an electrical schematic of a circuit for determining capacitance that can be used with the capacitive detector illustrated in FIGS. 1a-e.

With reference to FIG. 2, a preferred circuit for detecting the capacitance of the detector 10 is generally designated by the numeral 30. The detector 10 is represented as being electrically connected in series between electrical ground by the wire 13 and a reference capacitor 32 by the external end 16b. The detector 10 capacitor shown schematically in FIG. 2, of course, has one plate formed by the grounded conduit 12 and the other plate formed by the wire 16. The use of a reference capacitor provides a convenient capacitance value for the circuit 30 to measure when no liquid is present on the wire 16, however, use of the reference capacitor is largely a matter of design choice.

The circuit 30 preferably includes an operational amplifier 34 (hereinafter "op-amp" 34) configured to function as an inverting summing amplifier. A DC bias voltage 36 is applied to the inverting input 38 of the op-amp 34 through an input resistor 40. A feedback resistor 42 is connected across the inverting input 38 and the op-amp output terminal 44. For convenience the input resistor 40 and the feedback resistor 42 may be of the same value so that the op-amp acts as a unity gain amplifier with respect to the bias voltage 36.

The detector 10 and reference capacitor 32 are connected to the inverting input of the op-amp 34 by a serially connected diode 46 and inductor 48. The detector 10 and reference capacitor 32 are connected to the non-inverting input 50 of the op-amp 34 by a serially connected second diode 52 and a secondary winding 54 of a transformer 55.

A primary winding 56 of the transformer 55 is connected to an AC oscillator 58 that produces, for example, a 6 kilohertz sine wave voltage across the primary winding 56.

The two diodes 46,52 are connected to provide a positive half-wave rectified signal at the common diode node 60. The diode 46 provides DC isolation of the signal at node 60 from the virtual ground at the summing node 38. The inductor 48 functions as a low frequency filter that passes rectified AC signals from the detector 10 to the summing node 38.

A high frequency bypass capacitor 62 can be provided to shunt high frequency noise to ground. Also, the non-inverting input 50 is connected to ground so that the op-amp functions as an inverting voltage gain summing amplifier.

The circuit 30 operates as follows. The oscillator 58 applies an AC signal to the circuit via the transformer 55. The detector 10 and reference capacitor 32 in combination with the diode 52 forms a half-wave rectifier for the AC signal applied from the oscillator 58. The half-wave rectified signal generated at node 60 is filtered through the inductor 48 and summed with the bias voltage 36 at the summing node 38. The summing node 38 is, of course, the same node as the inverting input to the op-amp 34. The output voltage at the op-amp output terminal 44 is the sum of the bias voltage 36 and the voltage produced by the half-wave rectification of the AC signal. The DC voltage level produced by the half-wave rectifier is a function of the capacitance of the detector 10 added to the value of the reference capacitor 32. The magnitude of the bias voltage 36 and the amplitude of the applied AC signal from the oscillator can be adjusted, as well as the value of the reference capacitor 32, so that under a known condition of no liquid on the detector 10, the output 44 from the op-amp 34 is a convenient number such as zero volts. When liquid particles adhere to the wire 16, the capacitance between the wire and the conduit 14 will change and be detected as a change in the output voltage of the op-amp 34. The op-amp output voltage changes in relation to the change in capacitance of the detector 10 because the capacitance of the detector affects the DC voltage level produced by rectification of the applied AC signal.

The present invention also contemplates the methods described hereinabove with respect to the operation and use of the detector 10 for detecting the presence of liquid particles in a gaseous fluid conduit or pipe. These methods include the steps of connecting the conduit to electrical ground; placing a helically wound and insulated wire coil in the conduit along the longitudinal axis thereof and in contact with an inner surface of the conduit to form a capacitor with one plate being the conduit and another plate being the insulated wire; using the wire to obstruct flow of liquid particles along the inner surface of the conduit so that the liquid particles contact the wire; and measuring the capacitance between the wire and the conduit to determine the presence of liquid particles in the conduit. The methods may also include the step of placing a bend in the conduit to enhance the flow of liquid particles along the conduit inner surface, particularly in a weightless environment.

Those skilled in the art will appreciate that modifications will be apparent and still within the spirit and scope of the claimed invention. For example, the circuit 30 illustrated in FIG. 2 is only one of many types of circuits that can conveniently be used to measure the capacitance between the wire 16 and the conduit 14. Also, in situations where the conduit has a coated insulated inner surface 20, the wire 16 need not be insulated unless the liquid will degrade the wire material over a period of use. Furthermore, the helical shape of the wire 16 need not be precise. An important aspect rather, is that at least one loop of the wire contact the inner surface 20 of the conduct so that particles traveling along the surface 20 contact the wire. For example, in smaller pipes, the wire 16 can simply be twisted into a rather crudely shaped helix and still adequately contact particles moving along the conduit.

While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

I claim:

1. A liquid presence detector for a conductive conduit comprising a wire positioned within the conduit and having an end accessible from outside the conduit; said wire having a portion thereof in contact with a portion of an inner surface of the conduit with at least one of said wire portion and said portion of an inner surface of the conduit being insulated; said wire and conduit forming a capacitor; said wire portion contacting liquid traveling along said conduit inner surface; and means connectable to said accessible wire end and the conduit that detects capacitance of said wire and the conduit.

2. The liquid presence detector according to claim 1 wherein said conduit has a central longitudinal axis and said wire is insulated and wound with at least one loop in contact with and completely surrounding said conduit longitudinal axis.

3. The liquid presence detector according to claim 2 wherein the conduit includes at least one bend upstream from said wire.

4. The liquid presence detector according to claim 3 wherein the conduit is normally used in a weightless environment.

5. In combination, a liquid presence detector and an electrically grounded conductive pipe used to conduct gaseous fluid, said liquid presence detector comprising an insulated conductor inside a portion of the pipe, said insulated conductor contacting an inner surface of the pipe and contacting liquid traveling along said pipe inner surface; and means to measure capacitance between said insulated conductor and the pipe.

6. A liquid presence detector according to claim 5 wherein said insulated conductor is wound with at least one loop in contact with said pipe inner surface.

7. A liquid presence detector according to claim 6 wherein said insulated conductor is a helix with multiple loops contacting said inner surface and having an end extending outside the pipe.

8. A method for detecting liquid in a conductive gas pipe comprising the steps of:

a. connecting the pipe to electrical ground;

b. placing a conductor inside a portion of the pipe such that an outer surface of the conductor contacts the inner surface of said pipe portion but is insulated therefrom;

c. using said conductor to contact liquid traveling along said pipe inner surface; and d. measuring capacitance between the conductor and the pipe to detect the presence of liquid in the pipe.

9. The method for detecting liquid in a gas pipe according to claim 8 wherein the conductor is an insulated wire the step of placing an insulated wire loop inside a portion of the pipe includes the step of forming the wire into a generally helical shape.

* * * * *